United States Patent [19]

Pflugbeil et al.

[11] Patent Number: 4,510,314
[45] Date of Patent: Apr. 9, 1985

[54] PREPARATION OF 1-AZOLYL-3,3-DIMETHYL-1-PHENOXYBUTAN-2-OLS

[75] Inventors: Wolf-Dietrich Pflugbeil; Wolfgang Krämer, both of Wuppertal, Fed. Rep. of Germany

[73] Assignee: Bayer Aktiengesellschaft, Leverkusen, Fed. Rep. of Germany

[21] Appl. No.: 516,171

[22] Filed: Jul. 21, 1983

[30] Foreign Application Priority Data

Aug. 3, 1982 [DE] Fed. Rep. of Germany ....... 3228867

[51] Int. Cl.³ .................. C07D 233/60; C07D 249/08; C07D 233/61
[52] U.S. Cl. ..................................... 548/262; 548/341
[58] Field of Search ................................ 548/262, 341

[56] References Cited

U.S. PATENT DOCUMENTS 3,952,002  4/1976  Kramer et al. .................... 548/262
4,232,033  11/1980 Kramer et al. .................... 424/269

FOREIGN PATENT DOCUMENTS 0001414  4/1979  European Pat. Off. ............ 548/262
0011191  5/1980  European Pat. Off. ............ 548/341

OTHER PUBLICATIONS

Wildo, Organic Reactions, vol. II, (Roger Adams, Ed., Wiley, New York, 1944), pp. 180-182, 196-197.

Primary Examiner—Alton D. Rollins
Attorney, Agent, or Firm—Sprung, Horn, Kramer & Woods

[57] ABSTRACT

A process for the preparation of a 1-azolyl-3,3-dimethyl-1-phenoxybutan-2-ol of the formula

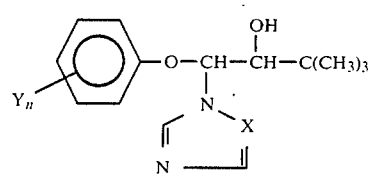

in which
X is a nitrogen atom or the CH group,
Y is halogen, alkyl, alkoxycarbonyl, nitro or optionally substituted phenyl, and
n is 0,1,2 or 3.

comprising reacting a 1-azolyl-3,3-dimethyl-1-phenoxybutan-2-one of the formula

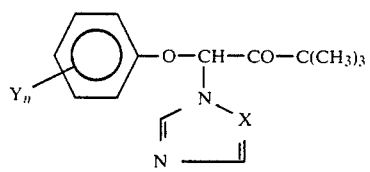

with a secondary alcoholate under pressure in the presence of a diluent. Advantageously the reaction is carried out at a temperature about 20° to 40° C. above the boiling point of the diluent which is a secondary alcohol, the alcoholate is aluminum isopropylate and is present in about 0.35 to 0.4 mol per mol of ketone, and the reaction is carried out under an excess pressure of about 1.5 to 5 bar.

9 Claims, No Drawings

PREPARATION OF 1-AZOLYL-3,3-DIMETHYL-1-PHENOXYBUTAN-2-OLS

The present invention relates to a new process for the preparation of known fungicidally active 1-azolyl-3,3-dimethyl-1-phenoxybutan-2-ols.

It has already been disclosed that 1-azolyl-3,3-dimethyl-1-phenoxybutan-2-ols are obtained if the corresponding keto derivatives are reduced by the Meerwein-Ponndorf-Verley reduction method using aluminum isopropylate in isopropanol (compare U.S. Pat. No. 4,232,033 and U.S. Ser. No. 095,000, filed Nov. 16, 1979), abandoned.

The Meerwein-Ponndorf-Verley reduction method has the disadvantage that this process involves an equilibrium reaction. This means the use of a relatively large excess of the reducing agent, and the removal of a reactant (for example acetone) from the equilibrium, in order to achieve the desired shift in the equilibrium required for the formation of the reduction product.

It has been found that the known 1-azolyl-3,3-dimethyl-1-phenoxybutan-2-ols of the formula

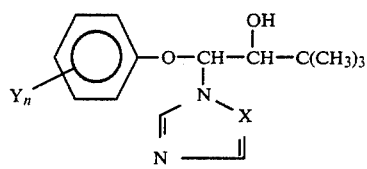

in which
X represents a nitrogen atom or the CH group,
Y represents halogen, alkyl, alkoxycarbonyl, nitro or optionally substituted phenyl and
n represents integers from 0 to 3,
are obtained if 1-azolyl-3,3-dimethyl-1-phenoxybutan-2-ones of the formula

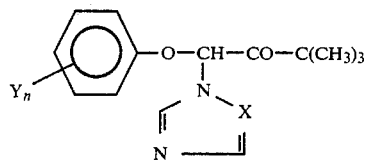

in which
X, Y and n have the meaning indicated above,
are reacted with secondary alcoholates in a pressure reaction in the presence of a diluent.

The compounds of the formula (I) possess two asymmetric carbon atoms; they can, therefore, exist in the two geometrical isomers, threo and erythro.

It must be described as surprising that, under the conditions of the process according to the invention, that is to say in a pressure reaction and without removing one reactant by distillation in order to displace the equilibrium in the desired manner, the Meerwein-Ponndorf-Verley reduction gives the end products in a very good yield and state of purity.

The process according to the invention has a number of advantages. The reaction according to the invention is carried out in a closed system, in which pressure and the high temperatures possible result in short reaction times with an equally good yield. In addition, a smaller excess of reducing agent is required. The pressure process according to the invention can thus be regarded as very cost-efficient, particularly with regard to its use on a semi-technical or technical scale.

The 1-azolyl-3,3-dimethyl-1-phenoxybutan-2-ols which can be prepared by the process according to the invention are defined in a general manner by the formula (I). In this formula Y preferably represents fluorine, chlorine, bromine or iodine, straight-chain or branched alkyl having 1 to 4 carbon atoms, alkoxycarbonyl having 1 or 2 carbon atoms in the alkyl part, nitro and phenyl which is optionally monosubstituted or disubstituted by identical or different substituents, in which connection the following may be mentioned as preferable substituents: fluorine, chlorine, bromine and methyl. X and the index n preferably represent the meanings indicated in the definition of the invention.

It is particularly preferable for $Y_n$ to represent p-chlorine and p-phenyl and for X to represent a nitrogen atom.

If, for example, 1-(4-chlorophenoxy)-3,3-dimethyl-1-(1,2,4-triazol-1-yl)-butan-2-one and aluminum isopropylate are used as the starting materials, the course of the reaction can be reproduced by the following equation:

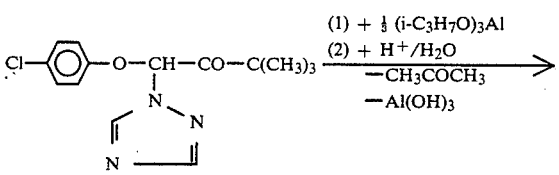

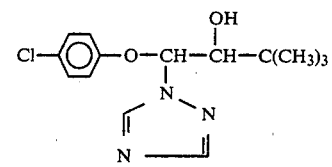

The 1-azolyl-3,3-dimethyl-1-phenoxybutan-2-ones to be used as starting materials in carrying out the process according to the invention are defined in a general manner by the formula (II). In this formula X, Y and the index n preferably represent the meanings which have already been mentioned preferentially in connection with the description of the compounds of the formula (I) which can be prepared in accordance with the invention.

The 1-azolyl-3,3-dimethyl-1-phenoxybutan-2-ones of the formula (II) are known (compare German Patent Specification No. 2,105,490 and U.S. Pat. No. 4,048,318.

The reduction according to the invention is carried out by means of secondary alcoholates. These preferably include the secondary alcoholates of aluminum such as, in particular, aluminum isopropylate and aluminum sec.-butylate.

Suitable diluents for the reaction according to the invention are preferably secondary alcohols, such as, in particular, isopropanol and sec.-butanol.

The reduction according to the invention is carried out under pressure, which can be varied within a fairly wide range. In general, the reaction is carried out at an excess pressure of 1 to 8 bar, preferably 1.5 to 5 bar.

The reaction temperatures in the process according to the invention can be varied within a fairly wide range. In general, the reaction is carried out within a temperature range which is 10° to 60° C., preferably 20° to 40° C., above the boiling point of the diluent used.

In carrying out the reaction according to the invention, it is preferable to employ about 1.05 to 1.2 equivalents of alcohol moiety, corresponding to 0.35 to 0.4 mol of aluminum alcoholate per 1 mol of ketone of the formula (II). The whole reaction mixture is then heated in a closed kettle until the desired temperature and the desired pressure have been established. After a reaction time of 2 to 6 hours, the reaction mixture is concentrated and the residue is hydrolyzed in a customary manner, such as, for example, by means of dilute sulphuric acid and isopropanol. Further working up is carried out in a customary manner.

The compounds which can be prepared in accordance with the invention are distinguished, as is known, by a very good fungicidal activity (compare U.S. Pat. No. 3,952,002 issued Apr. 20, 1976 and U.S. Pat. No. 3,940,414 issued Feb. 24, 1976, and U.S. Pat. No. 4,232,033).

The process according to the invention will be illustrated by means of the following preparation examples.

PREPARATION EXAMPLES

Example 1

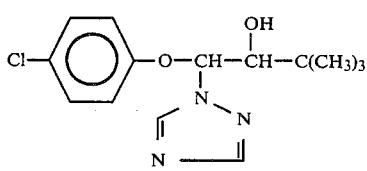

(Semi-technical scale)

2,000 liters of isopropanol, 600 kg of 1-(4-chlorophenoxy)-3,3-dimethyl-1-(1,2,4-triazol-1-yl)-butan-2-one and 200 kg of aluminum isopropylate are mixed by stirring in a 3,000 liter stirred kettle. The mixture is heated to the boil (80° C.), while stirring. The kettle is closed in a pressure-tight manner and is heated further until an internal temperature of 130° C. has been reached, which corresponds to a kettle pressure of 4 to 5 bar. The progress of the reaction is monitored by gas chromatography until complete reduction has been achieved. The reaction time is 2 to 3 hours. The contents of the kettle are cooled until normal pressure has been reached. The kettle is opened. Part of the solvent is removed by distillation (approximately 1,000 liters). A mixture of 3,000 liters of water and 160 kg of concentrated sulphuric acid is initially taken, at 20° C., in a 5,000 liter stirred kettle. The warm, approximately 70° C., residue from the distillation of the reaction mixture is added slowly, while stirring, and the reaction product crystallizes out. When the addition is complete, the suspension is cooled to 10° C. The crystals are removed on a stirred pressure filter and are washed and dried in vacuo at 50° C. This gives 574 kg (95% of theory) of 1-(4-chlorophenoxy)-3,3-dimethyl-1-(1,2,4-triazol-1-yl)-butan-2-ol having a threo content of 80% and a melting range of 108°-123° C.

Example 2

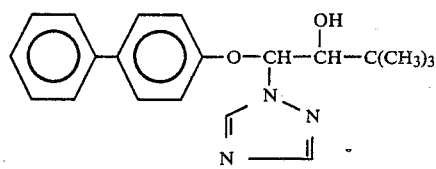

(Semi-technical scale)

2,000 liters of isopropanol, 637 kg of 1-(4-biphenylyloxy)-3,3-dimethyl-1-(1,2,4-triazol-1-yl)-butan-2-one and 200 kg of aluminum isopropylate are mixed by stirring in a 3,000 lit stirred kettle. The mixture is heated to the boil (80° C.), while stirring. The kettle is closed in a pressure-tight manner and is heated further until an internal temperature of 115° C. has been reached, which corresponds to a kettle pressure of 1.5 to 2 bar. The progress of the reaction is monitored by gas chromatography, until complete reduction has been achieved. The reaction time is 4 to 6 hours. The contents of the kettle are cooled until normal pressure has been reached. The kettle is opened. Part of the solvent is removed by distillation (approximately 1,000 liters). 1,050 kg of 15 percent strength sulphuric acid are initially taken (20° C.) in a second 3,000 liter stirred kettle. The warm, approximately 70° C., residue from the distillation of the reaction mixture is added, while stirring. After the addition, the mixture is stirred for one hour at 60° C. A liquid two-phase mixture is formed when employing this procedure. The phases are separated at 60° C. via a heated separating vessel. The organic phase is added slowly at 60° C., and while stirring, to a mixture of 2,000 liters of water and 45 kg of 45% strength sodium hydroxide solution which is initially taken, at 20° C., in a 5,000 liter stirred kettle. In the course of this the reaction product crystallizes. When the addition is complete, the contents of the kettle are cooled to 10° C. and the crystalline product is isolated on a stirred pressure filter. The filter cake is washed with water until it is neutral and is dried to constant weight in vacuo at 50° C. This gives 609 kg (95% of theory) of 1-(4-biphenylyloxy)-3,3-dimethyl-1-(1,2,4-triazol-1-yl)-butan-2-ol having a threo content of 85% and a melting range of 105°-131° C.

It will be understood that the specification and examples are illustrative but not limitative of the present invention and that other embodiments within the spirit and scope of the invention will suggest themselves to those skilled in the art.

What is claimed is:

1. A process for the preparation of a 1-azolyl-3,3-dimethyl-1-phenoxybutan-2-ol of the formula

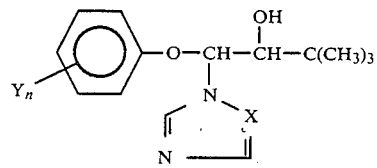

in which

X is a nitrogen atom or the CH group,

Y is halogen, alkyl, alkoxycarbonyl, nitro or phenyl which is optionally monosubstituted or disubstituted by fluorine, chlorine, bromine and/or methyl, and n is 0,1,2 or 3, comprising reacting a 1-azolyl-3,3-dimethyl-1-phenoxybutan-2-one of the formula

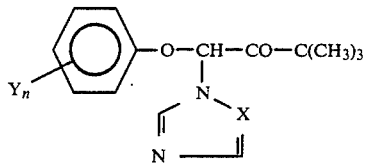

with an aluminum isopropylate or sec-butoxide under an excess pressure of about 1.5 to 5 bar in the presence of a diluent.

2. A process according to claim 1, in which

Y is fluorine, chlorine, bromine, iodine, alkyl having 1 to 4 carbon atoms, alkoxycarbonyl having 1 or 2 carbon atoms in the alkyl part, nitro, or phenyl which is optionally monosubstituted or disubstituted by fluorine, chlorine, bromine and/or methyl.

3. A process according to claim 1, in which $Y_n$ is a p-chlorine atom or a p-phenyl group, and X is a nitrogen atom.

4. A process according to claim 1, wherein the alcoholate is aluminum isopropylate.

5. A process according to claim 1, wherein the reaction is carried out at a temperature from about 10° to 60° C. above the boiling point of the diluent.

6. A process according to claim 1, wherein the reaction is carried out at a temperature about 20° to 40° C. above the boiling point of the diluent.

7. A process according to claim 1, wherein the diluent is a secondary alcohol.

8. A process according to claim 1, wherein about 1.05 to 1.2 equivalents of alcohol moiety are employed per mol of ketone.

9. A process according to claim 3, wherein the reaction is carried out at a temperature about 20° to 40° C. above the boiling point of the diluent which is a secondary alcohol, the alcoholate is aluminum isopropylate and is present in about 0.35 to 0.4 mol per mol of ketone.

* * * * *